United States Patent [19]

Bare

[11] Patent Number: 4,745,121

[45] Date of Patent: May 17, 1988

[54] PYRAZOLO[3,4-B]PYRIDINE-5-CARBOXAMIDES AND THEIR USE AS ANXIOLYTIC AGENTS

[75] Inventor: Thomas M. Bare, West Chester, Pa.

[73] Assignee: ICI Americas Inc., Wilmington, Del.

[21] Appl. No.: 774,905

[22] Filed: Sep. 11, 1985

[30] Foreign Application Priority Data

Oct. 4, 1984 [GB] United Kingdom ............... 84/25104

[51] Int. Cl.[4] ................... A61K 31/40; C07D 471/04; C07D 223/04

[52] U.S. Cl. .................................. 514/303; 546/119; 540/596; 540/597

[58] Field of Search .......................... 546/119; 514/303

[56] References Cited

U.S. PATENT DOCUMENTS

| | | |
|---|---|---|
| 3,755,340 | 8/1973 | Hoehn et al. ....................... 546/119 |
| 3,840,546 | 10/1974 | Hoehn et al. ....................... 546/119 |
| 3,966,746 | 6/1976 | Hoehn et al. ....................... 546/119 |
| 3,979,399 | 9/1976 | Hoehn et al. ....................... 546/119 |
| 4,511,568 | 4/1985 | Bare et al. ............................. 546/83 |
| 4,552,883 | 11/1985 | Bare ..................................... 546/119 |

OTHER PUBLICATIONS

Fieser, Reagents for Org. Synthesis, vol. I, pp. 78–79, 1967.
McOmie, Protective Groups In Org. Chemistry, pp. 61–63, 1973.
March, J. Adv. Org. Chem., pp. 382–383.
Morrison et al., Org. Chem., 3rd Ed., pp. 752–753.

*Primary Examiner*—John M. Ford
*Assistant Examiner*—J. Richter
*Attorney, Agent, or Firm*—Rosemary M. Miano

[57] ABSTRACT

This invention relates to pyrazolo[3,4-b]pyridine amides useful as anxiolytic agents.

5 Claims, No Drawings

PYRAZOLO[3,4-B]PYRIDINE-5-CARBOXAMIDES AND THEIR USE AS ANXIOLYTIC AGENTS

This invention relates to pyrazolo[3,4-b]pyridine amides which are anxiolytic agents.

According to the invention there is provided an amide derivative of the formula I:

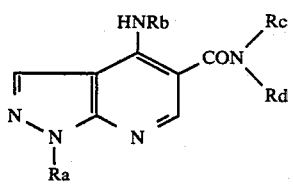

in which

Ra is selected from the group consisting of alkyl, alkenyl, alkynyl, haloalkyl, haloalkenyl, cyanoalkyls and ketoalkyls;

Rb is hydrogen, alkyl or alkanoyl;

Rc and Rd may be the same or different and are each independently selected from the group consisting of hydrogen, alkyl, cycloalkyl, cycloalkylalkyl, alkenyl, alkynyl, alkoxy, alkoxyalkyl, haloalkyl, haloalkenyl, phenyl, benzyl and thiazolyl, or Rc and Rd are joined to form, together with the nitrogen to which they are attached, a 4- to 7-membered ring which optionally contains a double bond;

and the 7-N-oxides thereof;

provided that if Ra is (1–3C)alkyl, at least one of Rc and Rd is (3–10C)alkenyl or (3–10C)alkynyl, and the pharmaceutically-acceptable acid-addition salts thereof, including those of the 7-N-oxides.

A particular value for Ra is (1–10C)alkyl, (3–10C)alkenyl, (3–10C)alkynyl, (1–10C)cyanoalkyl, (1–10C)ketoalkyl, (1–10C)haloalkyl or (3–10C)haloalkenyl, wherein each of the halo groups has at least one halogen selected from the group consisting of fluoro and chloro, preferably fluoro; Ra may be, for example, n-pentyl, 1-, 2- or 3-methylbutyl, 1- or 2-ethylbutyl, n-hexyl, 1-, 2-, 3- or 4-methylpentyl, n-heptyl, n-octyl, allyl, but-3-enyl, pent-4-enyl, 2-methylprop-2-enyl, pent-3-ynyl, pent-4-ynyl, hex-4-ynyl or hex-5-ynyl.

A particular value for Rb is hydrogen, (1–10C)alkyl or (1–10C)alkanoyl, for example hydrogen, ethyl, n-propyl, n-butyl, n-pentyl, acetyl, propionyl, butyryl or valeryl. It is preferred that Rb be hydrogen or (1–10C)alkanoyl.

A particular value for Rc or Rd is hydrogen, (1–10C)alkyl, (3–6C)cycloalkyl, (3–6C)cycloalkyl(1–6C)alkyl, (3–10C)alkenyl, (3–10C)alkynyl, (1–6C)alkoxy, (1–6C)alkoxy(2–6C)alkyl, (1–6C)haloalkyl, (1–6C)haloalkenyl, phenyl, benzyl or thiazolyl, for example, hydrogen, methyl, ethyl, n-propyl, i-propyl, n-butyl, n-pentyl, cyclopropyl, cyclobutyl, cyclohexyl, cyclopropylmethyl, cyclobutylmethyl, cyclohexylmethyl, 2-cyclopropylethyl, 2-cyclobutylethyl, 2-cyclohexylethyl, allyl, propargyl, but-2-ynyl, ethoxy, 2-methoxyethyl, 2,2,2-trifluoroethyl, 3,3-dichloroprop-2-enyl, phenyl, benzyl or thiazolyl.

A particular value for the ring formed when Rc and Rd are joined is an azetidine, pyrrolidine, piperidine or 3-pyrroline ring.

A particular acid-addition salt is one formed with hydrochloric, hydrobromic, sulfuric or nitric acid.

More particular selections of the compounds of the invention may be found in the following three categories listed according to their order of preference.

(1) The most preferred group of compounds are those in which Ra is (3–10C)alkenyl or (3–10C)alkynyl and Rc and Rd are each selected from the group consisting of hydrogen, (1–10C)alkyl, (3–6C)cycloalkyl, (3–6C)cycloalkyl(1–6C)alkyl, (3–10C)alkenyl and (3–10C)alkynyl.

(2) The next most preferred group of compounds are those in which Ra is (1–10C)alkyl and at least one of Rc and Rd are selected to be a (3–10C)alkenyl or (3–10C)alkynyl.

(3) A third group of compounds are those in which Ra is (4–5C)alkyl and both Rc and Rd are selected from the group consisting of hydrogen, (1–10C)alkyl, (3–6C)cycloalkyl and (3–6C)cycloalkyl(1–6C)alkyl, provided that for groups 1 and 2 Ra, Rc and Rd do not have any unsaturated carbon-carbon bonds at the "1" position.

A particularly preferred group of compounds are those of the formula I in group 1 in which Ra is alkynyl, with the most preferred compounds being those having a triple bond in the "3" or "4" position.

The most preferred compound is 4-amino-1-(pent-3-ynyl)-1H-pyrazolo[3,4-b]pyridine-5-N-(2-propenyl)carboxamide and its hydrochloride salt (Example 20).

Compounds of the formula I may be prepared by methods known in themselves for the manufacture of chemically-analogous compounds. Thus the following processes are provided as further features of the invention, Ra, Rb, Rc and Rd having the meanings stated above unless indicated otherwise.

(a) reaction of a compound of the formula II:

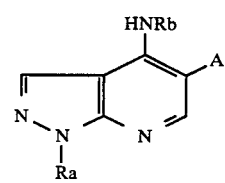

where A is an acid (—COOH) or an activated derivative thereof, for example ester, acid chloride (preferred), anhydride or acyl imidazole, with an amine of the formula RcRdNH;

(b) for those compounds in which Rb is alkanoyl, acylation of the compound of the formula I in which Rb is hydrogen;

(c) alkylation, alkenylation or alkynylation of a compound of the formula III:

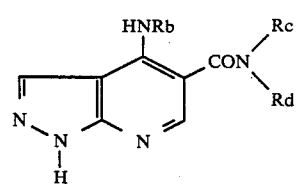

(d) reaction of a compound of the formula IV:

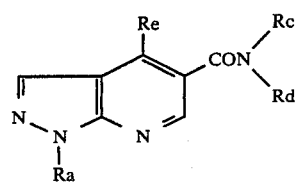

in which Re is a displaceable radical, for example, ethoxy, chloro, bromo, iodo with a compound of the formula Rb—NH$_2$; and whereafter, when the compound of formula I is obtained, for example, in the form of a free base and a pharmaceutically acceptable acid addition salt is required, the base may be reacted with an acid which affords a pharmaceutically acceptable anion.

The starting material of the formula II for use in process (a) may be prepared by alkylation, alkenylation or alkynylation of a compound of formula V:

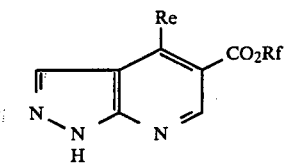

where Rf is (1–6C)alkyl, (for example, ethyl 4-ethoxy-H1-pyrazolo [3,4-b]pyridine-5-carboxylate) to give a compound of formula VI:

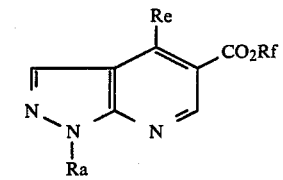

with subsequent reaction of the compound of Formula VI with an amine of the formula Rb—NH$_2$ and, if necessary, hydrolysis of the ester to form the corresponding acid (from which a suitable activated derivative such as an acid chloride may be prepared if required), for example as illustrated in Example 19.

The starting material of the formula III for use in process (c) may be prepared in a similar manner, but omitting the first alkylating, alkenylating or alkynylating step and reacting the acid or activated derivative with an appropriate amine to get a compound of formula III.

The compounds of material V may be prepared as follows: A compound of formula VII, where Rg is hydrogen or an alkyl, e.g., (1–6C)alkyl, is reacted with N-bromosuccinimide (NBS) to give a compound of formula VIII:

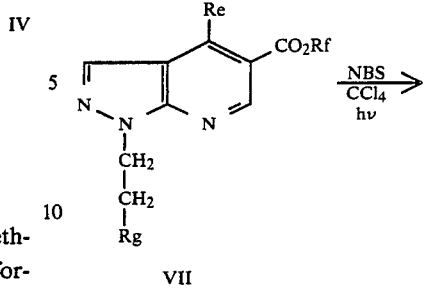

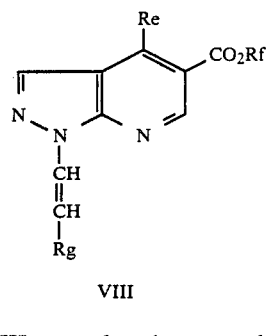

A compound of formula VIII may then be reacted under acidic or basic conditions (for example, Na$_2$CO$_2$ in water or aqueous hydrochloric acid in acetonitrile) to give a compound of formula V. Compounds of formula VII may be made by the methods described in U.S. Pat. No. 3,755,340 to Hoehn et al.

The starting material of the formula IV for use in process (d) may be prepared by hydrolysis of an ethyl 1-alkyl-, 1-alkenyl- or 1-alkynyl-1H-pyrazolo[3,4-b]pyridine-5-carboxylate derivative of formula VI carrying the group Re (for example, ethoxy) in the 4-position, followed by reaction of the 5-carboxylic acid, or an activated derivative thereof, with an amine of the formula RcRdNH in a process analogous to process (a).

As indicated above, the compounds of the present invention are anxiolytic agents. This activity may be demonstrated by the Shock-Induced Suppression of Drinking (Rats) Test (SSD) described in *Pharmacology Biochemistry and Behaviour*, 1980, Vol. 12, pp. 819–821. This test may be carried out as follows:

Male rats in the weight range of 200 to 220 g are deprived of water for 48 hours and deprived of food for 24 hours before testing. Normally, the rats are orally intubated (5 ml./kg.) with the selected concentration of test compound (based on mg./kg. body weight). Concentrations tested ranged from about 0.78 mg/kg to 50 mg/kg. The vehicle control group of rats is also intubated by mouth. A positive control group of rats is also orally administered a control dose of 18 mg./kg. of chlordiazepoxide. Random selection of the rats is utilized in dosing. The rats are returned to the cage for one hour. Sixty minutes after drug administration, the rat is quietly removed from its cage and the hind feet wiped with Signa electrode gel made by Parker Laboratories of Orange, N.J. When intraperitoneal (i.p.) administration is used, the protocol is identical except that the drugs are administered (with the selected dosage in a volume of 5 ml./kg.) 30 minutes prior to testing. The rat is placed on the floor in the chamber facing the licking tube. The animal is allowed 5 minutes to make 20 licking responses and then receives the first shock (0.5 mA). If this response does not occur, the animal is removed and eliminated from the study. If 20 licking responses are made, the animal is permitted an additional 3 minutes during which time each 20th lick is paired with a 0.5 mA shock. This period is automatically started, counted and terminated. The number of licks and shocks are recorded. The activity of the compound tested is evaluated by comparing the mean shocks of the group dosed with the test compound to both the mean shocks of the vehicle and positive control groups via a Students' t-test. In general, an increase in the number of shocks received compared to the control is indicative of the anti-conflict or anti-anxiety activity of the compound.

Compounds of this invention demonstrated activity in the SSD test.

According to a further feature of the invention there is provided a pharmaceutical composition which comprises an amide derivative of the invention in association with a pharmaceutically-acceptable diluent or carrier.

The pharmaceutical composition may, for example, be in a form suitable for oral, rectal or parenteral administration, for which purposes it may be formulated by means known to the art into the form of, for example, tablets, capsules, aqueous or oily solutions or suspensions, emulsions, dispersible powders, suppositories or sterile injectable aqueous or oily solutions or suspensions.

A preferred pharmaceutical composition of the invention is one suitable for oral administration in unit dosage form, for example a tablet or capsule which contains between 5 mg. and 500 mg. of the amide derivative, or one suitable for intravenous, intramuscular or subcutaneous injection, for example a sterile injectable containing between 0.1% and 10% w/w of the amide derivative.

The pharmaceutical composition of the invention will normally be administered to a mammal for relief of anxiety and tension in the same manner as that employed for chlordiazepoxide, due allowance being made in terms of dose levels for the potency and duration of action of the amide derivative of the invention relative to chlordiazepoxide. Thus each individual will receive an oral dose of between 0.5 mg. and 200 mg., and preferably between 0.5 mg. and 50 mg., of amide derivative, or an intravenous, subcutaneous or intramuscular dose of between 0.05 mg. and 50 mg., and preferably between 0.05 mg. and 10 mg., of the amide derivative, the composition being administered one to four times per day. The rectal dose will be approximately the same as the oral dose.

The invention is illustrated, but not limited, by the following Examples in which the temperatures are in degrees Centigrade and the following contractions are used: DMF (dimethyl formamide); Et (—CH$_2$CH$_3$); EtOAc (ethyl acetate); MeOH (methanol); EtOH (ethanol); ether (diethyl ether); THF (tetrahydrofuran); w/w (weight/weight), v/v (volume/volume); m.p. (melting point); g (grams); ml (milliliter(s)); decomp. (decomposition). Chemical symbols have their usual meanings unless otherwise indicated.

EXAMPLE 1

4-Amino-1-n-pentyl-1H-pyrazolo[3,4-b]pyridine-5-carboxamide (Formula I, Ra=n-pentyl, Rb=Rc=Rd=H)

A mixture of ethyl 4-chloro-1-n-pentyl-1H-pyrazolo[3,4-b]pyridine-5-carboxylate (this compound may be made as described in European Patent Publication No. 96995, for example, Example 11c) (24.88g.) and liquid ammonia (60 ml.) was heated in a stainless steel pressure vessel at 90°–100° for 12 hours. The excess ammonia was allowed to evaporate and the solid white residue was triturated with water. The collected solid (24 g.), a mixture of 4-amino ethyl ester and amide, was dissolved in a mixture of EtOH (210 ml.), sodium hydroxide (13.5 g.) and water (24 ml.) and the mixture heated at 45°–50° for 10 hours. The reaction mixture was evaporated and the residue dissolved in water and extracted with EtOAc and then with ether. The combined extracts were dried (MgSO$_4$), filtered, and the solvent evaporated. The residual solid was purified by chromatography on silica gel using MeOH/chloroform 7:93 v/v as eluant and the product was recrystallized from EtOH to give the title compound (1.23 g., 5.9%), m.p. 201°–201.9°.

EXAMPLE 2

4-Amino-1-n-pentyl-1H-pyrazolo[3,4-b]pyridine-5-n-propylcarboxamide (Formula I, Ra=n-pentyl, Rb=Rc=H, Rd=n-propyl)

To a stirred suspension of 4-amino-1-n-pentyl-1H-pyrazolo[3,4-b]pyridine-5-carboxylic acid (which may be prepared as described below or as described in European Patent Publication No. 96995, for example, Example 11e) (0.96g.) in chloroform (15 ml.) was added thionyl chloride (1.8 g.). The reaction mixture was stirred for 1 hour at room temperature then cooled in an ice bath and treated with n-propylamine (3.3 g.) with vigorous stirring. The mixture was allowed to warm to room temperature then washed with water until the washes were neutral. The organic layer was dried (MgSO$_4$) and the solvent evaporated. The residual solid was recrystallized from toluene to give the title compound (0.77 g., 72%), m.p. 142.8–144.8.

The starting material was prepared as follows. The aqueous layer from the NaOH hydrolysis in Example 1 was filtered through diatomaceous earth and acidified with acetic acid. The resulting precipitate was washed with water and air-dried to give 4-amino-1-n-pentyl-1H-pyrazolo[3,4-b]pyridine-5-carboxylic acid (17.01 g., 81%). A sample had a melting point of 253°–254° (decomp.) after recrystallization from EtOH.

EXAMPLES 3–6

The process described in Example 2 was repeated, using the appropriate amines, as starting materials, and the following compounds of the formula I, were obtained.

| Example | Ra | Rb | Rc | Rd | m.p. ° |
| --- | --- | --- | --- | --- | --- |
| 3 | n-pentyl | H | cyclopropyl | H | 151.5–152.7 |
| 4 | n-pentyl | H | allyl | H | 138.8–139.8 |
| 5 | n-pentyl | H | propargyl | H | 169–170.5 |
| 6 | n-pentyl | H | CH$_2$-cyclopropyl | H | 143–144 |
| 6-1 | n-pentyl | H | benzyl | H | 159.8–160.6 |

EXAMPLE 7

4-Amino-1-n-pentyl-1H-pyrazolo[3,4-b]pyridine-5-(N-propyl-N-methyl) carboxamide hydrochloride (Formula I as a hydrochloride, Ra=n-pentyl, Rb=H, Rc=n-propyl, Rd=methyl)

To a stirred suspension of 4-amino-1-n-pentyl-1H-pyrazolo[3,4-b]pyridine-5-carboxylic acid (0.96 g) in chloroform was added thionyl chloride (0.69 g). The reaction mixture was stirred for 1 hour at room temperature, then cooled in an ice-bath and treated with N-methylpropylamine (1.71 g.). The mixture was allowed to warm to room temperature then washed with water until the washings were neutral. The organic layer was dried (MgSO4) and evaporated and the residue was purified by chromatography on silica gel using hexane/EtOAc 1:2 v/v as eluant. The purified product was dissolved in EtOH (4 ml.) and ethereal HCl added. The resulting precipitate was collected, washed with EtOH/ether and dried to give the title compound (1.03 g, 78%), m.p. 151.5°–153°.

EXAMPLES 8–11

The process described in Example 7 was repeated using the appropriate amines as starting materials and isolating the product as the hydrochloride salt. The following compounds of the formula I, as their hydrochloride salts, were thus prepared.

| Example | Ra | Rb | Rc | Rd | m.p.° |
|---|---|---|---|---|---|
| 8 | n-pentyl | H | ethyl | methyl | 143–144 |
| 9 | n-pentyl | H | ethyl | ethyl | 177–178 |
| 10 | n-pentyl | H | allyl | methyl | 111–138 (decomp.) |
| 11 | n-pentyl | H | propargyl | methyl | 203.5–204.5 |

EXAMPLE 12

4-Amino-1-n-pentyl-1H-pyrazolo[3,4-b]pyridine-5-N-(2-methoxyethyl)carboxamide (Formula I, Ra=n-pentyl, Rb=Rc=H, Rd=2-methoxyethyl)

To a stirred suspension of 4-amino-1-n-pentyl-1H-pyrazolo[3,4-b)]pyridine-5-carboxylic acid (1.03 g.) in chloroform (15 ml.) was added thionyl chloride (0.73 g). After stirring at room temperature for 2 hours the resulting cloudy solution was added to a stirred ice-cold solution of 2-methoxyethylamine (1.87 g) in chloroform (25 ml). After stirring for 15 minutes the reaction mixture was poured into water and extracted with chloroform. The combined extracts were washed with water, dried (MgSO4) and evaporated and the residue recrystallized from toluene/hexane to give the title compound (0.98 g, 77%), m.p. 114°–115°.

EXAMPLES 13–18

The process described in Example 12 was repeated, using the appropriate amines as starting materials, and the following compounds of the formula I, as their hydrochloride salts, were prepared.

| Example | Ra | Rb | Rc | Rd | m.p.° |
|---|---|---|---|---|---|
| 13 | n-pentyl | H | methyl | H | 273–274 |
| 14 | n-pentyl | H | methyl | methyl | 207–208 |
| 15 | n-pentyl | H | ethyl | H | 238–242.5 |
| 16 | n-pentyl | H | n-propyl | ethyl | 195–196 |
| 17 | n-pentyl | H | allyl | allyl | 198–200 |
| 18 | n-pentyl | H | propargyl | propargyl | 164–166 |

EXAMPLE 19 a.
4-Amino-1-(pent-3-ynyl)-1H-pyrazolo[3,4-b]pyridine-5-N-(2-propynyl)carboxamide (Formula I, Ra=pent-3-ynyl, Rb=Rc=H, Rd =propargyl)

To a stirred suspension of 4-amino-1-(pent-3-ynyl)-1H-pyrazolo[3,4-b]pyridine-5-carboxylic acid (0.8 g.) in chloroform (15 ml.) was added thionyl chloride (0.58 g.). The mixture was stirred at room temperature for 1 hour, then cooled in an ice bath, and this solution of acid chloride was then treated with propargylamine (1.1 g.). The thick reaction mixture was allowed to warm to room temperature, diluted with EtOAc and poured into water. The organic layer was separated, washed with water, dried (MgSO4) and evaporated. The residue was purified by chromatography on a short column of silica gel using EtOAc as eluant. The product was recrystallized from toluene/EtOAc to give the title compound (0.69 g, 74%), m.p. 192.0°–193.1°.

b. Ethyl 4-ethoxy-1-vinyl-1H-pyrazolo[3,4-b]-pyridine-5-carboxylate

A suspension of ethyl 1-ethyl-4-ethoxy-1H-pyrazolo[3,4-b]pyridine-5-carboxylate (which may be prepared as described in U.S. Pat. No. 3,755,340, for example, Example 1c) (14.24 g.) and N-bromosuccinimide (21.2 g.) in carbon tetrachloride (109 ml.) was stirred and heated under reflux while being irradiated with a sun lamp (Westinghouse 250 watt). After 1.5 hours the mixture was cooled (ice-bath) and filtered. The filtrate was washed with aqueous sodium bicarbonate and water, dried (MgSO4) and evaporated to give ethyl 4-ethoxy-1-vinyl-1H-pyrazolo[3,4-b]pyridine-5-carboxylate as a yellow oil.

c. Ethyl 4-ethoxy-1H-pyrazolo[3,4-b]pyridine-5-carboxylate

A solution of the 1-vinyl derivative of Example 19b in THF (112 ml.) was treated with a saturated aqueous sodium carbonate solution (67 ml.) and water (69 ml.). The solution was vigorously stirred for 28 hours at room temperature and the precipitated solid collected. The solid was washed with water, air-dried and recrystallized from EtOAc to give the title compound, m.p. 187.2°–187.8°.

d. Ethyl 4-ethoxy-1-pent-3-ynyl-1H-pyrazolo[3,4-b]pyridine-5-carboxylate

A mixture of the ethyl-4-ethoxy-1H-pyrazolo[3,4-b]pyridine-5-carboxylate of Example 19c (8.13 g.), pulverized anhydrous potassium carbonate (14.3 g.) and 1-bromo-3-pentyne (10.7 g.) in dry DMF (58 ml.) was stirred at 55°–60° for 4.5 hours. Additional quantities of 1-bromo-3-pentyne (5.3 g.) and potassium carbonate (14.3 g.) were added after 1 hour. The mixture was cooled and filtered and the filtrate evaporated at 45°–50°. The residue was diluted with water and extracted with ether and EtOAc. The combined extracts were washed with water, dried (MgSO4) and evaporated. The residue was purified by chromatography on silica gel using EtOAc/hexane 1:1 v/v as eluant to give the title compound, m.p. 93°–95°, after recrystallization from toluene.

e. Ethyl 4-amino-1-(pent-3-ynyl)-1H-pyrazolo-[3,4-b]pyridine-5-carboxylate (Formula II, Ra=pent-3-ynyl, Rb=H, A=—CO₂Et)

A mixture of the 1(pent-3-ynyl) derivative of Example 19d (7.6 g.), EtOH (10 ml.) and liquid ammonia (60 ml.) was heated to 75°–80° in a stainless steel pressure vessel for 12 hours. The vessel was allowed to cool and excess ammonia allowed to evaporate. The residue was triturated with water (100 ml.) and the resulting solid air-dried to give the title compound, m.p. 195.8°–196.6°.

f. 4-Amino-1-(pent-3-ynyl)-1H-pyrazolo[3,4-b]pyridine-5-carboxylic acid (Formula II, Ra=pent-3-ynyl, Rb=H, A=—COOH)

A stirred solution of the 4-amino derivative of Example 19e (6.1 g.) in EtOH (55 ml.) containing sodium hydroxide (3.6 g.) and water (6.6 ml.) was heated at 45°–50° for 10 hours. The reaction mixture was concentrated and the residue dissolved in water (100 ml). This solution was washed with ether, filtered through diatomaceous earth and the pH adjusted to 6 with acetic acid. The resulting precipitate was collected, washed with water and dried over $P_2O_5$ in vacuo to give the title compound, m.p. 233°–236° (decomp.), after recrystallization from EtOH/water.

EXAMPLE 20 a. 4-Amino-1-(pent-3-ynyl)-1H-pyrazolo[3,4-b]pyridine-5-N-(2-propenyl)carboxamide (Formula I, Ra=pent-3-ynyl, Rb=H, Rc=allyl, Rd=H)

To a stirred suspension of 0.80 g of 4-amino -1-(pent-3-ynyl)-1H-pyrazolo[3,4-b]pyridine-5-carboxylic acid as made in Example 19f in 15 ml. of chloroform was added thionyl chloride (0.58 g). The mixture was stirred at room temperature for 1 hr., then cooled in an ice bath and this solution of acid chloride treated with allylamine (1.1 g). The reaction mixture was allowed to warm to room temperature, diluted with EtOAc and poured into water. The organic layer was separated, washed with water, dried (MgSO4) and evaporated. The residue was purified by chromatography on a short column of silica gel using EtOAc as the eluant. The product was recrytallized from toluene/EtOAc to give the title compound (0.74 g., 80%) as white crystals, m.p. 180.5°–181.5°.

Calculated for $C_{15}H_{17}N_5O$: C, 63.59; H, 6.05; N, 24.72.

Found: C, 63.77; H, 6.06; N, 24.67.

b. 4-Amino-1-(pent-3-ynyl)-1H-pyrazolo[3,4-b]pyridine-5-N-(2-propenyl)carboxamide hydrochloride (Formula I as a hydrochloride, Ra=pent-3-ynyl, Rb=H, Rc=allyl, Rd=H)

Ethereal HCl was added to a solution of 4-amino-1-(pent-3-ynyl)-1H-pyrazolo[3,4-b]pyridine-5-N-allylcarboxamide 10 g) obtained by the method of Example 20a in 10 ml. of warm EtOH. A precipitate formed and was collected, washed with ether, and air-dried to give 1.0 g of white crystals. Recrystallization from ethanol gave 0.80 g. of the title compound as white crystals, m.p. 214°–214.8°.

Calculated for $C_{15}H_{17}N_5O.HCl$: C, 56.34; H, 5.67; N, 21.90.

Found: C, 56.28; H, 5.72; N, 21.83.

EXAMPLE 21

4-Amino-1-(pent-3-ynyl)-1H-pyrazolo-[3-4-b]pyridine-5-N-cyclopropylmethylcarboxamide

(Formula I, Ra = pent-3-ynyl, Rb = Rd = H, Rc = —CH₂—◁)

The process described in Example 19 was repeated, using cyclopropylmethylamine instead of propargylamine. The melting point of the compound obtained was 183.8°–185.0°.

EXAMPLE 22

4-Amino-1-(pent-3-ynyl)-1H-pyrazolo[3,4-b]pyridine-5-(N-2-propynyl-N-methyl)carboxamide hydrochloride (Formula I as a hydrochloride, Ra=pent-3-ynyl, Rb=H, Rc=propargyl, Rd=methyl)

To a cooled chloroform solution of the acid chloride prepared as in Example 19a from 0.8 g. of acid, was added N-methylpropargylamine (1.8 g.). The mixture was allowed to warm to room temperature, poured into water and extracted with chloroform. The combined extracts were washed with water, dried (MgSO4) and evaporated. The residual oil was dissolved in a minimum of EtOH, the solution filtered and to the filtrate was added ethereal HCl. Recrystallization of the precipitate from EtOH/ether gave the title compound (0.59 g., 54%), m.p. 179.8°–181.8°.

EXAMPLES 23-24

The process described in Example 22 was repeated, using the appropriate amines as starting materials, and the following compounds of the formula I, as their hydrochloride salts, were prepared.

| Example | Ra | Rb | Rc | Rd | m.p.° |
|---|---|---|---|---|---|
| 23 | pent-3-ynyl | H | n-propyl | methyl | 199–204 (decomp.) |
| 24 | pent-3-ynyl | H | allyl | methyl | 174–176.4 |

EXAMPLES 25-26

The process described in Example 12 was repeated, using the appropriate amines as starting materials, and the following compounds of the formula I were prepared, as listed in Table I.

TABLE I

| Example | Ra | Rb | Rc | Rd | m.p.° | Formula | Calculated C | H | N | Found C | H | N |
| --- | --- | --- | --- | --- | --- | --- | --- | --- | --- | --- | --- | --- |
| 25 | n-pentyl | H | —CH$_2$C≡CCH$_3$ | H | 132.9–133.8 | C$_{16}$H$_{21}$N$_5$O | 64.19 | 7.07 | 23.39 | 64.34 | 7.02 | 23.38 |
| 26 | n-pentyl | H | —CH$_2$CH=CCl$_2$ | H | 166.8–167.8 | C$_{15}$H$_{19}$Cl$_2$N$_5$O | 50.57 | 5.38 | 19.66 | 50.61 | 5.31 | 19.86 |

EXAMPLE 27

4-Amino-1-(pent-3-ynyl)-1H-pyrazolo-[3,4-b]pyridine5-N-propylcarboxamide (Formula I, Ra=pent-3-ynyl, Rb=Rd=H, Rc=propyl)

The process described in Example 19 was repeated using propylamine as starting material to prepare the title compound. The compound had a melting point of 184.2°–185.8°.

Calculated for C$_{15}$H$_{19}$N$_5$O: C, 63.14; H, 6.71; N, 24.54.

Found: C, 63.16; H, 6.68; N, 24.49.

EXAMPLE 28 a.

4-n-Butylamino-1-n-pentyl-1H-pyrazolo[3,4-b]-pyridine-5-N-(2-propenyl)carboxamide (Formula I, Ra=n-pentyl, Rb=n-butyl, Rc=allyl, Rd=H)

To a stirred suspension of 1.02 g of 4-n-butylamino-1-n-pentyl-1H-pyrazolo[3,4-b]pyridine-5-carboxylic acid in 10 ml. of chloroform was added 0.5 g. of thionyl chloride. The resulting solution was stirred at room temperature for 2 hr. and then added to a cold stirred solution of 0.86 g of allylamine in 20 ml. of chloroform. After stirring for 15 min., the resulting mixture was poured into water and the organic layer separated, washed with water and dilute aqueous sodium bicarbonate, and dried over MgSO$_4$. The mixture was filtered and concentrated to leave 1.17 g of a tan solid, which was recrystallized from toluene/hexane 1:2 (v/v) to give 1.00 g (87%) of the title compound as white needles, m.p. 105°–108°. was as follows:

Calculated for C$_{19}$H$_{29}$N$_5$O: C, 66.44; H, 8.51; N, 20.39.

Found: C, 66.32; H, 8.42; N, 20.32.

b. Ethyl 4-n-butylamino-1-n-pentyl-1H-pyrazolo[(3,4-b]pyridine-5-carboxylate (Formula II, Ra=n-pentyl, Rb=n-butyl, A=CO$_2$Et)

A solution of 5.00 g of ethyl 4-chloro-1-n-pentyl-1H-pyrazolo[3,4-b]pyridine-5-carboxylate (this compound may be prepared as described in European Patent Publication No. 96995) and 3.09 g of n-butylamine in 15 ml. of toluene was heated at 85°–95° for 4 hr. The reaction mixture was cooled, diluted with ether, and washed several times with water. After drying over MgSO$_4$, the ether solution was concentrated to leave 5.77 g of a light brown oil. This oil was chromatographed over silica gel using acetone/hexane 5:95 (v/v) as the eluant. The fractions containing the product were combined and concentrated to give 5.34 g (95%) of the product as a light yellow oil. For characterization a small portion was converted to its HCl salt as white crystals with a melting point of 160°–161°.

tyl-1H-pyrazolo[3,4-b]pyridine-5-carboxylic acid (Formula II, Ra=n-pentyl, Rb=n-butyl, A=—COOH)

c.

4-n-Butylamino-1-n-pentyl-1H-pyrazolo[3,4-b]pyridine-5-carboxylic acid (Formula II, Ra=n-pentyl, Rb=n-butyl, A=—COOH)

A solution of 4.03 g of the amino ester of Example 28b and 1.93 g of sodium hydroxide in 30 ml of ethanol containing 3.5 ml water was warmed at 45° for 2 hr. and then concentrated to remove most of the ethanol. The residue was dissolved in 50 ml of water and the resulting solution acidified with acetic acid. The resulting mixture was extracted with several portions of ethyl acetate and methylene chloride. The combined extracts were dried (MgSO$_4$). filtered, and concentrated to leave a white solid. Recrystallization of this solid from ethanol gave 3.65 g (91%) of the title compound as white plates, m.p. 154°–155°.

EXAMPLE 29 a.

4-Amino-1-(pent-4-ynyl)-1H-pyrazolo[3,4-b]pyridine-5-N-(2-propenyl)-carboxamide (Formula I, Ra=pent-4-ynyl, Rb=H, Rc=allyl, Rd=H)

To a stirred solution of 1.08 g of the amino acid of Example 29d in 20 ml of DMF was added 0.79 g of 1,1'-carbonyldiimidazole. After stirring the reaction mixture at room temperature for 3 hr., 0.76 g of allylamine was added and the resulting solution allowed to stir for 1 hr. The reaction mixture was poured into water and the resulting mixture extracted with EtOAc. The combined extracts were washed with water and brine, dried (MgSO$_4$). filtered, and concentrated to leave 0.90 g of a light yellow oil which slowly crystallized. Recrystallization from toluene gave 0.64 g (51%) of the title compound as white crystals, m.p. 117.5°–119°.

Calculated for C$_{15}$H$_{17}$N$_5$O: C, 63.58; H, 6.05; N, 24.72.

Found: C, 63.50; H, 5.96; N, 24.86.

b.

Ethyl-4-ethoxy-1-(pent-4-ynyl)-1H-pyrazolo[3,4-b]pyridine-5-carboxylate

A mixture of 3.78 g of ethyl 4-ethoxy-1H-pyrazolo[3,4-b]pyridine-5-carboxylate, 3.90 g of 1-iodo-4-pentyne, and 6.68 g of pulverized anhydrous potassium carbonate in 27 ml of dry DMF was stirred at 50°–60° for 1 hr. The mixture was cooled, poured into water, and the resulting mixture extracted with EtOAc. The combined extracts were washed with water and brine, dried (MgSO$_4$), filtered, and concentrated to leave 5.42 g of a dark oil which slowly crystallized. This material was chromatographed over silica gel using EtOAc/hexane 1:2 (v/v) as the eluant to give 3.03 g (62%) of the title compound as a white solid. A small quantity was recrystallized from toluene to give white crystals, m.p. 84°–85.5°.

c.

Ethyl-4-amino-1-(pent-4-ynyl)-1H-pyrazolo[3,4-b]-pyridine-5-carboxylate (Formula II, Ra=pent-4-ynyl, Rb=H, A=—CO$_2$Et)

A mixture of the compound of Example 29b (2.87 g) in 80 ml of ethanol saturated with ammonia in a glass-lined stainless steel pressure vessel was heated at 105°–110° for 14 hr. The vessel was allowed to cool and the reaction mixture was concentrated to leave 2.61 g of a light yellow solid. Recrystallization of this material from toluene/hexane gave 1.64 g (63%) of the title compound as pale yellow crystals, m.p. 132.5°–133.5°.

d. 4-Amino-1-(pent-4-ynyl)-1H-pyrazolo[3,4-b]pyridine-5-carboxylic acid (Formula II, Ra=pent-4-ynyl, Rb=H, A=—COOH)

A stirred solution of the above compound of Example 29c (1.64 g) in EtOH (15 ml) containing sodium hydroxide (0.99 g) and water (2 ml) was heated at 45°–55° for 2 hr. The cooled reaction mixture was then concentrated to remove most of the EtOH and the residue dissolved in water. The resulting solution was acidified with dilute aqueous HCl whereupon a precipitate formed. The precipitate was collected, washed with water, air-dried and then dried over $P_2O_5$ in vacuo to give 1.03 g (70%) of the title compound as a white solid, m.p. 214° (decomp.).

EXAMPLE 30 a. 4-Amino-1-(pent-4-enyl)-1H-pyrazolo[3,4-b]pyridine-5-N-(2-propenyl)-carboxamide (Formula I, Ra=pent-4-enyl, Rb=Rd=H, Rc=allyl)

To a stirred solution of 1.08 g of the amino acid of Example 30d in 20 ml of DMF was added 0.86 g of 1,1'-carbonyldiimidazole. After stirring the reaction mixture at room temperature for 3 hr., 0.76 of allylamine was added and the resulting solution allowed to stir at room temperature overnight. The reaction mixture was poured into water and extracted with EtOAc. The combined extracts were washed with water and brine, dried ($MgSO_4$), filtered, and concentrated to leave 1.50 g of a tacky crystalline solid. Recrystallization from toluene gave 0.85 g (68%) of the title compound as white crystals, m.p. 123°–124°.

Calculated for $C_{15}H_{19}N_5O$: C, 63.14; H, 6.71; N, 24.55.

Found: C, 63.38; H, 6.69; N, 24.29.

b. Ethyl 4-ethoxy-1-(pent-4-enyl)-1H-pyrazolo[3,4-b]pyridine-5-carboxylate

A mixture of 5.00 g of ethyl 4-ethoxy-1H-pyrazolo-[3,4-b]pyridine-5-carboxylate, 3.96 g of 1-bromo-4-pentene, and 8.83 g of pulverized anhydrous potassium carbonate in 36 ml. of anhydrous DMF was stirred at room temperature for 1 hr. and then at 55°–60° for 2 hr. The mixture was cooled, poured into water, and extracted with EtOAc. The combined extracts were washed with water and brine, dried ($MgSO_4$), filtered and concentrated to leave 6.81 g of a dark semi-solid mass. This material was chromatographed over silica gel using hexane/EtOAc 2:1 (v/v) as the eluant to give 4.34 g. (67%) of the title compound as a light tan solid. A small quantity was recrystallized from hexane to give tan crystals, m.p. 61°–62°.

c. Ethyl 4-amino-1-(pent-4-enyl)-1H-pyrazolo[3,4-b]-pyridine-5-carboxylate (Formula II, Ra=pent-4-enyl, Rb=H, A=—CO₂Et)

A mixture of the compound of Example 30b (4.14 g) in 80 ml. of EtOH saturated with ammonia was heated in a stainless steel measure vessel at 80°–100° for 12 hr. The vessel was allowed to cool and the reaction mixture was concentrated to leave 3.72 g (99%) of the title compound as a tan solid. A small quantity was recrystallized from toluene/hexane to give white plates, m.p. 130°–131°.

d. 4-Amino-1-(pent-4-enyl)-1H-pyrazolo[3,4-b]pyridine-5-carboxylic acid (Formula II, Ra=pent-4-enyl, Rb=H, A=—COOH)

A stirred solution of the 4-amino compound of example 30c (3.52 g) in EtOH (32 ml) containing sodium hydroxide (2.09 g) and water (4.25 ml) was heated at 45°–55° for 2 hr. The cooled reaction mixture was concentrated and the residue dissolved in water. The resulting solution was acidified with dilute aqueous HCl wherever a tan precipitate formed. The precipitate was collected and washed with water, air-dried, and then dried in vacuo over $P_2O_5$ to give 2.28 g of the title compound as a tan solid.

EXAMPLE 31

4-Amino-1-(pent-4-enyl)-1H-pyrazolo[3,4-b]pyridine-5-N-methyl-N-(2-propynyl)-carboxamide hydrochloride (Formula I as a hydrochloride, Ra=pent-4-enyl, Rb=H, Rc=propargyl, Rd=methyl)

To a stirred solution of 1.00 g of 4-amino-1-(pent-4-enyl)-1H-pyrazolo-[3,4-b]pyridine-5-carboxylic acid, as made by the method described in Example 30d, in 18 ml of DMF was added 0.80 g of 1,1'-carbonyldiimidazole. After stirring the reaction mixture at room temperature for 3 hr. 0.82 g of N-methylpropargylamine was added and the resulting solution allowed to stir at room temperature for 3 days. The reaction mixture was poured into water and extracted with EtOAc. The combined extracts were washed with water and brine, dried ($MgSO_4$). filtered, and concentrated to leave a brown oil. The oil was dissolved in 15 ml. of EtOH and acidified with ethereal HCl whereupon a white precipitate formed. The precipitate was collected, washed with EtOH/ether and then ether, and air-dried to give 0.94 g (70%) of the title compound as white crystals, m.p. 202°–203°.

Calculated for $C_{16}H_{19}N_5O \cdot HCl$: C, 57.56; H, 6.04; N, 20.98.

Found: C, 57.37; H, 6.15; N, 20.89.

EXAMPLE 32 a. 4-Amino-7-oxo-1-n-pentyl-1H-pyrazolo[3,4-b]pyridine-5-N-(2-propenyl)-carboxamide hydrochloride (Formula I as an 7-N-oxide and hydrochloride, Ra=n-pentyl, Rb=Rd=H, Rc=—CH₂CH=CH₂)

A mixture of 0.98 of the allylamide of Example 32c in 60 ml of EtOH saturated with ammonia was heated at 60°–70° in a stainless steel pressure vessel for 12 hr. The vessel was allowed to cool and the contents concentrated to leave 0.86 g of a tan solid. This material was chromatographed over silica gel using 2.5% MeOH in chloroform to give 0.61 g of a white solid, which was dissolved in 15 ml of EtOH and acidified with ethereal HCl. A white precipitate formed and was collected, washed with EtOH/ether, and air-dried to give 0.58 g (58%) of the title compound as white plates, m.p. 232°–237° (decomp.).

Calculated for $C_{15}H_{21}N_5O_2 \cdot HCl$: C, 53.01; H, 6.53; N, 20.61.

Found: C, 53.01; H, 6.67; N, 20.48.

b.
4-Ethoxy-7-oxo-1-n-pentyl-1H-pyrazolo[3,4-b]pyridine-5-carboxylic acid

A solution of 5.00 g of ethyl 4-ethoxy-7-oxo-1-n-pentyl-1H-pyrazolo[3,4-b]pyridine-5-carboxylate (this compound may be made as described in U.S. Pat. No. 4,511,568) in EtOH (40 ml) containing sodium hydroxide (0.75 g) and water (4 ml) was stirred at room temperature for 45 min. The reaction mixture was concentrated and the residue dissolved in 250 ml of water. The resulting solution was acidified with acetic acid whereupon a precipitate formed. The precipitate was collected, washed with water, and partially air-dried. Recrystallization from EtOH gave 3.25 g (71%) of the title compound as white plates, m.p. 173° (decomp.).

c.
4-Ethoxy-7-oxo-1-n-pentyl-1H-pyrazolo[3,4-b]pyridine--5-N-(2-propenyl)-carboxamide To a stirred suspension of the carboxylic acid of Example 32b (1.10 g) in 22 ml of DMF was added 0.67 g of 1,1'-carbonyldiimidazole. After stirring the reaction mixture at room temperature for 1 hr., 0.64 g of allylamine was added and the resulting solution stirred for 15 min. The reaction mixture was poured into water and the resulting mixture extracted with EtOAc. The combined extracts were washed with water and brine, dried (MgSO4), filtered, and concentrated to leave 1.01 g (81%) of the title compound as a white solid. A portion of the material was recrystallized from toluene/hexane to give pale yellow crystals, m.p. 112°–143°.

EXAMPLE 33
Ethyl 4-amino-1-n-pentyl-1H-pyrazolo[3,4-b]pyridine-5-hydroxamate (Formula I, Ra=n-pentyl, Rb=H, Rc=OEt, Rd=H)

To a stirred solution of 1.1 g of 4-amino-1-n-pentyl-1H-pyrazolo[3,4-b]pyridine-5-carboxylic acid and 0.56 g of triethylamine in 35 ml of MeOH was added a solution of 1.43 g of diphenylcarbamylpyridinium chloride in 5.6 ml of MeOH. After stirring for 20 min., the reaction mixture was cooled in an ice bath and added to a cold stirred solution of ethoxyamine which was prepared by adding 3.32 ml of a 25% methanolic sodium methoxide solution to a solution of 1.42 g of ethoxyamine hydrochloride in 10 ml of MeOH. The resulting mixture was stirred at room temperature for 1.5 hr. and then concentrated. The residue was diluted with 60 ml of water and the resulting mixture extracted with ether. The combined extracts were dried (MgSO4), filtered, and concentrated to give 1.98 g of an amber oil which was chromatographed over silica gel using ether as the eluant. The fractions containing the product were combined and concentrated to leave 0.92 g of a white foam. The foam was induced to crystallize by dissolving it in hot toluene containing a small amount of chloroform and cooling, whereupon crystals precipitated. These were collected, washed with cold toluene and hexane, and air-dried to give 0.69 g (53%) of the title compound as white crystals, m.p. 142.3°–144.2°.

Calculated for $C_{14}H_{21}N_5O_2$: C, 57.72; H, 7.27; N, 24.04.

Found: C, 57.92; H, 7.32; N, 24.32.

EXAMPLE 34
1-(Pent-3-ynyl)-4-propionamido-1H-pyrazolo[3,4-b]pyridine-5-N-(2-propenyl)-carboxamide (Formula I, Ra=pent-3-ynyl, Rb=—COCH2CH3, Rc=allyl, Rd=H)

To a stirred suspension of sodium hydride (1.10 g of a 50% suspension in nujol washed free of nujol with hexane) in dry DMF (90 ml) was added 2.94 g of 4-amino-1-(pent-3-ynyl)-1H-pyrazolo[3,4-b]pyridine-5-N-(2-propenyl)-carboxamide. After 45 min. of stirring, this solution was added to a stirred solution of 13.5 g of propionic anhydride in 60 ml of dry DMF. The reaction mixture was stirred for 5 min. and then quenched carefully by adding 5 ml of water. The resulting solution was partially concentrated (about one-third of DMF removed) and then poured into water and extracted with ether. The combined ether extracts were filtered to remove a small quantity of a precipitate which formed, dried (MgSO4), filtered and concentrated to give 3.27 g of a tacky yellow solid. This material was chromatographed over silica gel using EtOAc/hexane 4:5 (v/v) as the eluant. In addition to the desired product (0.58 g), 1.15 g of the starting allylamide was also obtained. The desired material was recrystallized from toluene to give 0.23 g (6.5%) of the title compound as white crystals, m.p. 157.5°–158.7°.

Calculated for $C_{18}H_{21}N_5O_2$: C, 63.70; H, 6.24; N, 20.63.

Found C, 63.95; H, 6.33; N, 20.61.

What is claimed is:

1. A compound of Formula I

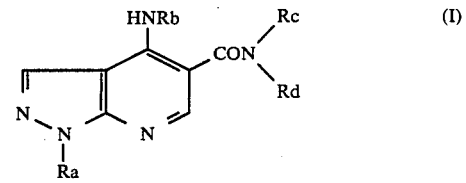

wherein Ra is pent-3-ynyl, Rb and Rd are each hydrogen, and Rc is allyl, or the hydrochloride salt thereof.

2. A compound of Formula I:

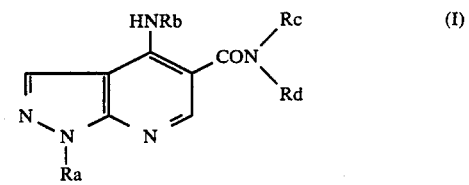

wherein
Ra is pent-3-ynyl or pent-4-ynyl;
Rb is hydrogen or propionyl;
Rc and Rd are each selected from a group consisting of hydrogen, (1–10C)alkyl, (3–6C)cycloalkyl, (3–6C)cycloalkyl(1–6C)alkyl, (3–10C)alkenyl and (3–10C)alkynyl, provided that Rc and Rd do not have any unsaturated carbon-carbon bonds at the "1" position, and wherein at least one of Rc and Rd is hydrogen;
or a 7-N-oxide thereof;
or a pharmaceutically-acceptable acid addition salt of said compound or its 7-N-oxide.

3. A compound as claimed in claim 2 wherein

Rb is hydrogen; and Rc and Rd are each selected from a group consisting of hydrogen, propyl, allyl, propargyl, but-2-ynyl, and cyclopropylmethyl.

4. An anxiolytic pharmaceutical composition comprising a compound of claim 2 in an amount sufficient to affect anxiolytic activity in a mammal in association with a non-toxic pharmaceutically-acceptable diluent or carrier.

5. A method of treating anxiety in a living mammal comprising administering to the mammal an anti-anxiety effective amount of a composition of claim 4.

* * * * *

UNITED STATES PATENT AND TRADEMARK OFFICE
CERTIFICATE OF CORRECTION

PATENT NO. : 4,745,121

DATED : MAY 17, 1988

INVENTOR(S) : THOMAS M. BARE

It is certified that error appears in the above-identified patent and that said Letters Patent is hereby corrected as shown below:

Column 9, line 11, "1(pent" should read as "1-(pent".
Column 10, line 1, "10 g)" should read as "(1.0g)".
Column 11, line 9, "pyridine5-" should read as "pyridine-5-".
Column 11, lines 62-63, delete "tyl-1H-pyrazolo[3,4-b] pyridine-5-carboxylic acid (Formula II, Ra=n-pentyl, Rb=n-butyl, A=—COOH)".

Signed and Sealed this

Eighth Day of November, 1988

Attest:

DONALD J. QUIGG

*Attesting Officer*  *Commissioner of Patents and Trademarks*